US00PP22627P2

(12) United States Plant Patent
Gossett

(10) Patent No.: US PP22,627 P2
(45) Date of Patent: Apr. 3, 2012

(54) ***HOSTA* PLANT NAMED 'AQUAMARINE'**

(50) Latin Name: *Hosta hybrida*
Varietal Denomination: Aquamarine

(75) Inventor: Gary J. Gossett, Portland, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 3 days.

(21) Appl. No.: 12/927,267

(22) Filed: Nov. 10, 2010

(51) Int. Cl.
*A01H 5/00* (2006.01)

(52) U.S. Cl. ..... Plt./353

(58) Field of Classification Search ..... Plt./353
See application file for complete search history.

*Primary Examiner* — Susan McCormick Ewoldt
(74) *Attorney, Agent, or Firm* — Klarquist Sparkman, LLP

(57) ABSTRACT

A new and distinct *Hosta* plant characterized by large, glaucous, blue green leaves with dark petioles and leaf bases. In the spring the leaves are dark purple tinted on top. *Hosta* 'Aquamarine' has violet flowers in late summer into fall.

1 Drawing Sheet

Botanical denomination: *Hosta hybrida.*
Variety designation: 'Aquamarine'.

BACKGROUND OF THE INVENTION

The present invention relates to a new and distinct cultivar of *Hosta,* botanically known as a *Hosta hybrida,* and hereinafter will be referred to by its cultivar name 'Aquamarine'. *Hosta* is in the family Hostaceae. The plant is the culmination of a breeding program for dark leaf base, dark petiole *Hosta.* It was bred in Canby, Oreg. using unpatented proprietary parents. The exact parents are unknown.

Compared to *Hosta* 'Purple Haze', the new cultivar has bluer foliage, darker petioles, and a dark leaf base rather than a blue green leaf base.

SUMMARY OF THE INVENTION

This new cultivar is unique in the combination of large, glaucous, blue green leaves with dark petioles and leaf bases. In the spring the leaves are dark purple tinted on top. *Hosta* 'Aquamarine' has violet flowers in late summer into fall.

This new cultivar has been reproduced only by asexual propagation (division and tissue culture). Each of the progeny exhibits identical characteristics to the new cultivar. Asexual propagation by tissue culture using standard micropropagation techniques with lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph shows a three-year-old plant in late spring.

DETAILED PLANT DESCRIPTION

The following is a detailed description of the new *Hosta* cultivar based on observations of a two-year-old specimen grown in the ground in an open air shade house with 50% shade in Canby, Oreg. in early September. Canby is Zone 8 on the USDA Hardiness map. Temperatures range from a high of 95 degrees F. in August to 32 degrees F. in January. Normal rainfall in Canby is 42.8 inches per year. The color descriptions are all based on The Royal Horticultural Society Colour Chart, $5^{th}$ edition.

Plant:

*Type.*—Herbaceous perennial.
*Hardiness.*—USDA Zones 4 to 9.
*Size.*—Grows to 33 cm wide and 12 cm tall from the top of the soil to the top of the foliage.
*Form.*—Clumping to form a mound.
*Number of crowns per plant.*—About 6.
*Number of leaves per crown.*—7.

Leaf:

*Type.*—Simple.
*Shape.*—Ovate.
*Arrangement.*—Basal rosette.
*Blade length.*—Grows to 15 cm.
*Blade width.*—Grows to 9.5 cm.
*Margins.*—Entire.
*Apex.*—Cirrhose.
*Base.*—Truncate.
*Petiole.*—7 cm long and 7 mm to 12 mm wide, clasping, glaucous, sulcate, inner and outer surface Greyed Green 189B heavily spotted Greyed Purple N186A.
*Texture.*—Leathery.
*Surface texture.*—Glaucous on both surfaces.
*Venation.*—Average of 6 pairs of veins, camptodrome pattern, impressed on upper surface and raised on lower surface.
*Color.*—Topside between Greyed Green 189A and 189B, base and along margin speckled Greyed Purple N186A; bottom side between Green N138C and Greyed Green 189C.

Inflorescence:

*Type.*—Self cleaning; terminal raceme.
*Number of flowers per raceme.*—About 20.
*Size of inflorescence.*—14 cm long and 12 cm wide.
*Peduncle description.*—Grows to 29 cm long and 5 mm wide, glaucous, Greyed Green 188A.

*Pedicel description*.—14 mm long and 1.5 mm wide, glabrous, Greyed Green 194A tinted Greyed Purple N186A on bottom ⅔ and Violet 85A on top ⅓.

*Floral bracts*.—One at the base of each pedicel, at a 30 degree angle from the horizontal, grows to 2.5 cm long and 15 mm wide, becoming progressively smaller going up, ovate, margins membranous and entire, acute, clasping, cupping upward; bottom side Yellow Green 147A tinted Violet Blue N92A, inside Yellow Green 147B tinted Violet Blue N92A.

*Bloom time*.—August to October in Canby, Oreg.

*Lastingness of inflorescence*.—6 to 8 weeks.

Flower Bud:

*Size*.—34 mm long and 12 mm wide.

*Shape*.—Irregularly oblong, narrowing at the base.

*Surface texture*.—Glabrous.

*Color*.—Closest to Violet 85B.

Flower:

*Type*.—Perfect.

*Shape*.—Campanulate tubular.

*Size*.—Average 5.5 cm long and 2 cm wide.

*Color*.—Inside and outside Violet 85A.

*Corolla description*.—6 overlapping tepals, lobes overlapping, 40 mm long and 20 mm wide overall (tube 12 mm long and 4.5 mm wide), glabrous inside and out except inside lobe tip where pubescent; outer tepal lobes 26 mm long and 8 mm wide 28 mm long and 12 mm wide, oblanceolate, margins entire, tip obtuse, base attenuate; inner tepals obovate, margins entire, tip obtuse, base narrowing abruptly.

*Pistil description*.—42 mm long, ovary 5 cm long and 3 mm wide, Yellow Green 146C, style 37 mm long, White 155A, stigma Yellow 11A.

*Stamen*.—6, filaments 4.7 cm long, Yellow Green 149D, anthers 5 mm long and 2.5 mm wide, Brown 200D, pollen none, male sterile.

*Fragrance*.—None.

Fruit: None, sterile.

Seed: None.

Pest and diseases: Snail and slugs are the main problems on *Hosta*. This new cultivar has leathery, glaucous leaves and appears to be less appealing to slugs. No susceptibility or resistance to diseases or other pests has been observed.

I claim:

1. A new and distinct hybrid *Hosta* plant as herein shown and described.

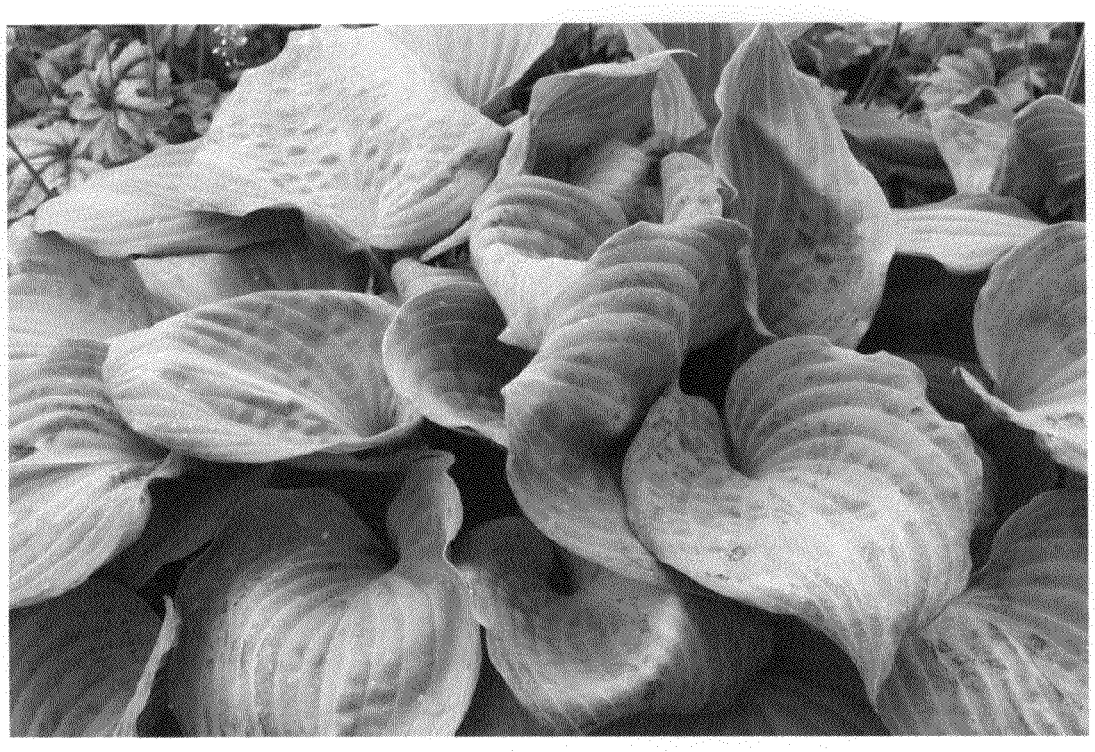

* * * * *